United States Patent [19]
Long et al.

[11] Patent Number: 6,029,084
[45] Date of Patent: Feb. 22, 2000

[54] THERAPEUTIC FIELD GENERATOR

[75] Inventors: Sharon Alice Jane Long; Stephen John Walpole, both of Bexhill-on-Sea, United Kingdom

[73] Assignee: Alistair Ross MacNicol, East Sussex, United Kingdom

[21] Appl. No.: 08/930,826

[22] PCT Filed: Apr. 15, 1996

[86] PCT No.: PCT/GB96/00908

§ 371 Date: Jan. 2, 1998

§ 102(e) Date: Jan. 2, 1998

[87] PCT Pub. No.: WO96/32158

PCT Pub. Date: Oct. 17, 1996

[30] Foreign Application Priority Data

Apr. 13, 1995 [GB] United Kingdom ............... 9507664

[51] Int. Cl.[7] .................................................. A61N 1/00
[52] U.S. Cl. ............................ 607/2; 607/45; 607/62
[58] Field of Search ........................... 607/2, 47, 45, 607/62, 70

[56] References Cited

U.S. PATENT DOCUMENTS 5,871,517  2/1999  Abrams et al. ..................... 607/45

FOREIGN PATENT DOCUMENTS

| 0500983 | 2/1991 | European Pat. Off. . |
| 1371236 | 6/1963 | France . |
| 2547505 | 12/1994 | France . |
| 1764831 | 8/1968 | Germany . |
| 2156679 | 10/1985 | United Kingdom . |

*Primary Examiner*—Jeffrey R. Jastrzab
*Attorney, Agent, or Firm*—Pollock, Vande Sande & Amernick

[57] ABSTRACT

An electric or electromagnetic field generator for therapeutic use. A heartbeat signal produced by a user is monitored to derive a signal indicative of the frequency of the user's heartbeat. A generator creates an electric or electromagnetic field based on a combined signal derived from a first signal dependent on the determined heartbeat frequency, and a second signal stimulating the brain activity of the user. The device may be worn by the user, on an ongoing basis. The second signal may be modified to provide a train of pulses having a width substantially equal to a neuron depolarization pulse to improve the user's response to the signal.

9 Claims, 3 Drawing Sheets

FREQUENCY 1         HEART BEAT FREQUENCY

THERAPEUTIC FIELD GENERATOR

FIELD OF THE INVENTION

This invention relates to a therapeutic field generator, particularly generating an electromagnetic or electric field. The invention is particularly but not exclusively concerned with generators adapted to be portable, self-contained units, and worn by a person.

An example of an earlier device for generating electromagnetic fields can be found in our earlier UK Patent GB-2156679-B to which further reference should be made. The device is based on the theory that exposure to certain electromagnetic fields can have a therapeutic effect. A patient undergoes a spectrum analysis of brain electrical activity (EEG) which will locate gaps or minima at certain frequencies. The electromagnetic field generator attempts to stimulate electrical activity by applying external electromagnetic fields at frequencies corresponding to these gaps. Devices made in accordance with GB-2156679-B offer relief for migraine, hypertension, lower back pain, premenstrual tension and ME, depending upon the frequencies stimulated.

The earlier device uses two separate oscillators generating a first signal comprising pulses at a fixed frequency of 1.15 Hz (corresponding to a central frequency of a group of brain waves called Delta-waves) and a second signal comprising pulses at a frequency which corresponds to a 'gap' frequency. The frequency of the second signal may be selected by bank of switches connected to capacitors. The two signals are then mixed and output to an antenna as an electromagnetic wave.

One of the problems with the above device is that the electromagnetic wave generated is not readily accepted by some users and so does not stimulate desired electrical activity. The present invention is based on the appreciation that acceptance can be improved with a first, carrier, signal adjusted to correspond to the heartbeat rate of the wearer. Furthermore it has been determined that a better response is obtained with a shorter pulse width, which substantially corresponds to the width of a neuron depolarisation pulse of ca. 125 microseconds. Exposure to low levels of electromagnetic radiation is contra-indicated in some individuals. Accordingly, the present invention envisages apparatus adapted to produce electromagnetic fields, preferably fields having a very small magnetic component. By producing a substantially pure electric field of a specific shape, the signal is carried into the wearer's system without the need for a magnetic component.

SUMMARY OF INVENTION

In its broadest sense, the present invention provides an electric or electromagnetic field generator for therapeutic use, comprising:

monitoring means for determining the heartbeat frequency of a user;

a generator and an output means adapted to generate and output an electric or electromagnetic field corresponding to a combined signal derived from a first signal and a second signal, wherein the frequency of the first signal is dependent upon the determined heartbeat frequency, and the second signal is related to the brain activity of the user.

The device is typically provided with a strap or lanyard to allow it to be worn close to the body of the user.

Electromagnetic or electric fields generated by the above apparatus have a much higher rate of acceptance by the human body due to the linking of the first signal in the users heartbeat and as a result achieves better results in stimulating brain electrical activity.

The monitoring means for determining the frequency of the heartbeat is typically a field effect type microphone or an infrared array comprising an infrared emitter and an infrared detector. This may be worn on the body separately from the generator, for example at the wrist or other pulse sites.

Preferably the second signal is a train of pulses each having a width substantially equal to the width of a neuron depolarisation pulse. Advantageously the width of each pulse is in the range 100 to 150 microseconds, more advantageously in the range 120 to 130 microseconds and most advantageously the width of each pulse is substantially 125 microseconds.

Preferably the train of pulses is generated at frequencies up to 100 Hz.

An electromagnetic field output may be produced by means of a coil and preferably generates a field strength in the range 200–300 nT (nano Tesla), and advantageously 250 nT, for effective treatment.

Where a magnetic component is contra-indicated in a patient, fields of around 43 pT or less are achievable and preferred.

Typically, the electric or electromagnetic field generator means comprises a microcontroller connected to the heartbeat monitoring means. The field generator may further comprise memory means, preferably a non-volatile memory, coupled to the microcontroller, for storing values representative of the different frequencies of the pulse train. The memory preferably holds a sequence of value in the range of 0–100 Hz and the microcontrollable accesses the memory sequentially acquiring the values in turn so that the frequency of the second signal pulse train is changed depending on the required value. Advantageously, the non-volatile memory is an Electrically Erasable Read Only Memory (EEROM) programmable by the microcontroller.

Preferably the generator further comprises means adapted to receive control signals from a remote transmitter and more preferably the microcontroller uses the control signals to programme the memory. Suitably, such means are incorporated into the microcontroller or heartbeat monitor.

DESCRIPTION OF THE FIGURES

The above and other aspects of the present invention will now be described, by way of example only, with reference to the accompanying drawings in which.

DESCRIPTION OF THE PREFERRED EMBODIMENT

Figure 1:
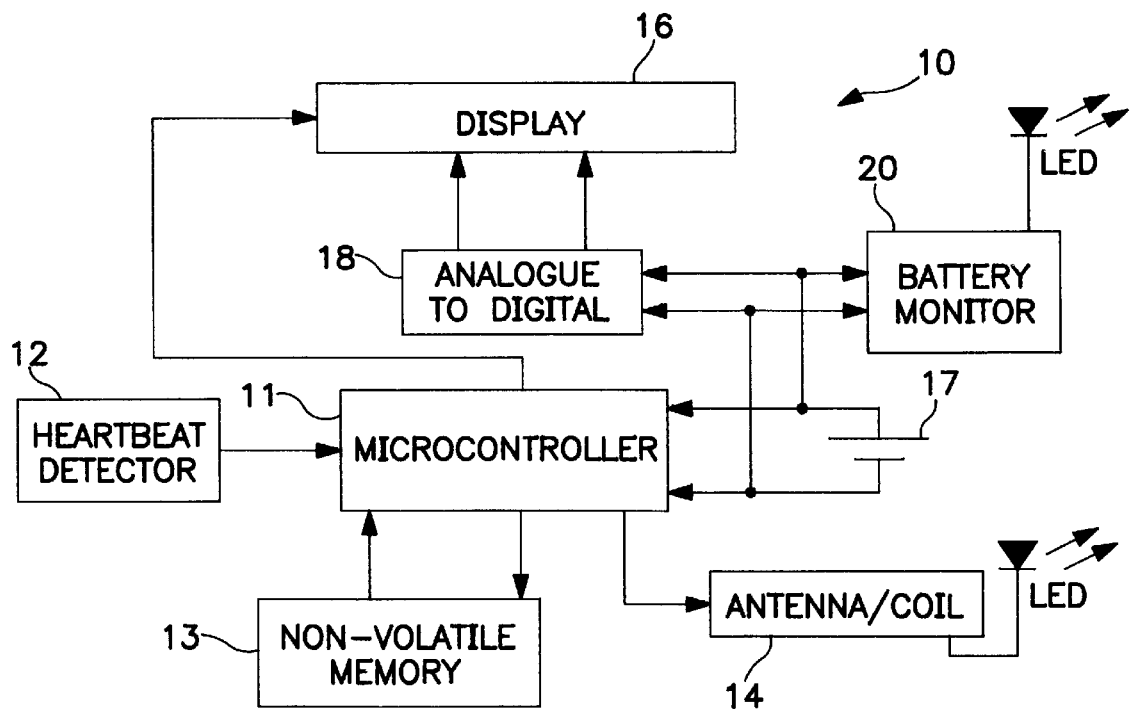
FIG. 1 is a block diagram showing the main features of a generator apparatus in accordance with the present invention.

Referring now to FIG. 1, an embodiment of an electric or electromagnetic field generator 10 in accordance with the present invention has a microcontroller 11 having an input/output connected to a heartbeat detector 12; an input/output connected to a memory 13; and an output connected to an antenna or coil 14. The microcontroller 11 receives a signal from the heartbeat detector 12 and generates a first signal 21 at frequency substantially the same as the heart rate. The microcontroller 11 reads a value from the memory 13 and generates a second signal 22 comprising a train of pulses having a width of 125 μsec at a frequency corresponding to the value obtained from memory. The microcontroller 11 then mixes the first and second signals and output the combined signal 23 as an electromagnetic or electric wave at the antenna or coil 14.

Figure 2:
FIG. 2 shows a representation of a first signal, second signal and combined signal respectively.
Figure 2:
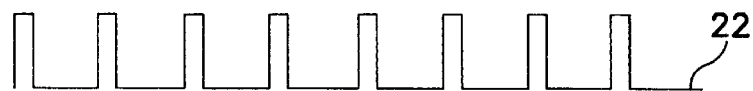
Figure 2:

The typical waveforms of the first signal 21, second signal 22 and combined signal 23 are shown in FIG. 2. It can be seen in this embodiment that the first signal 21 is effectively superimposed on the second signal 22 to form the combined signal 23.

In one embodiment, the heartbeat detector 12 is an infrared array consisting of a light emitting diode (LED) and a photo detector. The infrared array is periodically accessed by the microcontroller 11 which switches on the LED; blood cells absorb the light and re-emit infrared light signals dependent on the heart or pulse rate of the wearer. The photodetector converts the infrared signal to an electric signal and outputs it to the microcontroller.

In an alternative embodiment, the heartbeat detector 12 includes a field effect type microphone. The microphone is periodically accessed by the microcontroller 11. The heartbeat sounds picked up by the microphone are, of course, dependent upon the heart or pulse rate of the wearer.

If the microcontroller 11 fails to receive a signal from the heartbeat detector 12 it uses a default value of 70 beats per minute (1.167 Hz) to approximate an average heartbeat rate. The heartbeat rate is only periodically checked to converse battery power as the LED or microphone circuit will probably consume more power than the rest of the circuit combined.

The heartbeat monitor 12 may also be adapted to receive control signals from a remote transmitter (not shown). These control signals are used to initialise the generator for an individual user's requirements. The remote transmitter may be a separate unit or may be part of an EEG (Electroencephalogram).

Figure 4:
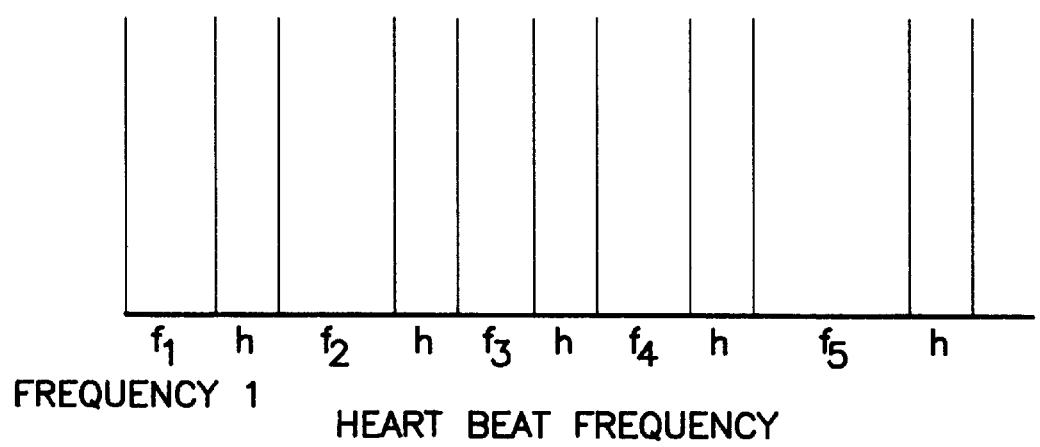
FIG. 4 illustrates a combined output wave of heartbeat and EEG analysis derived frequencies.

The data values stored in the memory 13 represent particular frequencies required in the treatment and are typically found by EEG analysis of the patient's brain electrical activity, by scanning for missing or reduced frequencies in areas known by the clinician to be implicated in an ailment. The microcontroller 11 accesses a frequency value and a pulse or train of pulses at that frequency $f_1$ is generated for a fixed duration. The next value in memory is accessed and a pulse or train of pulses at the new frequency $f_2$ is generated. In this way a series of pulses or pulse trains is generated to be combined alternately with the first (heartbeat dependent) signal h and output as an electric or electromagnetic wave, each pulse or pulse train corresponding to a different value as stored in the memory 13. A typical example of a generated pulse train is shown in FIG. 4.

The memory 13 is of a non-volatile type such that data is retained even on power loss—typically a non-volatile Electrically Erasable Read Only Memory EEROM programmable by the microcontroller. As mentioned above, the microcontroller receives remote control signals via the heart beat monitor and uses these signals to program the memory on initialisation. Alternatively, the memory 13 may be preprogrammed with the relevant frequencies after a spectrum analysis of the person. Once initialised the memory will retain the programming indefinitely and even in the event of a power loss it may only be changed on re-initialisation.

The memory may also be programmed with other information, for instance the duration of each pulse train, which can be varied to exposure of the user to certain frequencies for longer. It may also hold data for the wearer's name, address and doctor's name. The amount of data stored depends on the size of the memory but typically a total of 200 or so different frequency values can be stored.

In another embodiment the microcontroller 11 includes a real time clock and data is stored corresponding to when the EMF waves are to be generated, for instance during certain seasons or time cycles.

Figure 3:
FIG. 3 illustrates a suitable form of antenna for producing an electric field.

The microcontroller 11 drives the antenna or coil such that the electromagnetic field produced is in the range of 200 to 300 nT. A field strength of 250 nT has been found to be particularly effective. A suitable electric field antenna, ideally etched in copper on the same printed circuit board as the rest of the control circuit, is shown in FIG. 3. Such an antenna produces a field in the region of 43 pT as it consist of the equivalent of just 2.5 turns, rather than 300 or so turns as might be provided to give an electromagnetic field of the strength described above. Furthermore, this small magnetic effect is further reduced by effectively splitting the coil into two halves which are 'wound' in opposite directions, thereby producing a cancelling effect. It has been found that this form of antenna does appear to prevent the device from adversely affecting magnetic field sensitive patients.

The generator includes a display 16 to indicate correct operation. The display may be a liquid crystal display (LCD) or series of light emitting diodes pulsed by the microcontroller 11 under normal operating conditions.

As shown in FIG. 1, the antenna or coil 14 is preferably provided with an indicator 21 to indicate correct operation of the output means 14.

The generator 0 is suitably battery-powered, for example, by a lithium battery 17 for long life. The battery's condition may be monitored and displayed on a bar graph type display on the LCD 16. Alternatively or additionally a proprietary battery monitor 20 can be used. The digital bar graph is driven by an analogue to digital converter 18 connected to the battery 17 and/or the battery monitor circuit illuminates a red LED if the battery 17 falls below a preset minimum voltage.

The device is typically housed in a compact waterproof housing which is fixed to a body by means of a strap or chain and can be worn on the wrist, arm or leg. A separate interface may be built into the device to facilitate the connection of a data logger to the device. This would be used to record the heart rate changes of the wearer over a period of time and would be useful for monitoring a response to the device.

EXAMPLE

Figure 5:
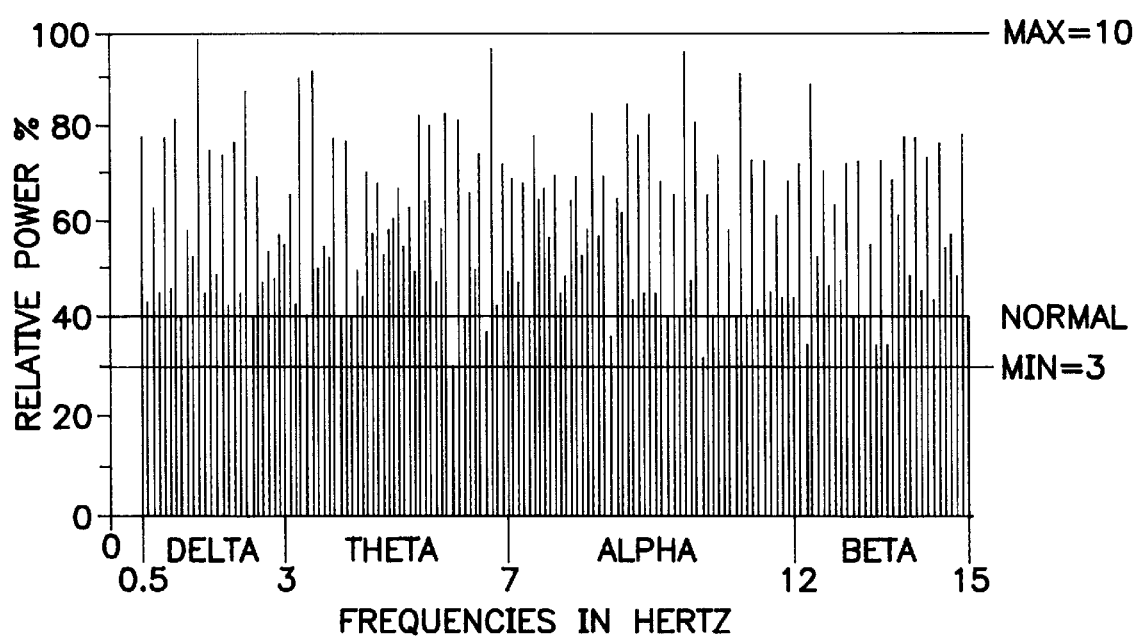
FIG. 5 illustrates an EEG analysis of a patient.

A male patient of 24 years of age presented with panic attacks. The symptoms were shaking, an accelerated heart rate of over 140 beats per minutes, dizziness and hyperventilating. These would occur for from ten minutes upto two hours every three to four days. The patient also had difficulty sleeping. A spectral analysis of EEG over a five minute period whilst the patient was not suffering an attack was taken (FIG. 5). From the analysis, it was decided that the following frequencies would help his condition: −1.2 Hz for sleep; 3.4 & 2.4 Hz for anxiety; 6 Hz for neurotransmitter imbalance; 8.8, 9.8 & 10.4 Hz for stress; and 12.2 Hz to help slow down the heartbeat at rest.

The field generator was programmed to produce a pulse of each frequency in turn, followed by a pulse at the patient's heart rate. As the pulse train was linked to the patient's heart rate, which to begin with was never very stable, the treatment was noticeably effective within three days and subsequent attacks have stopped, returning only when the batteries in the device used in this example were exhausted. The patient's sleep pattern also normalised.

We claim:

1. An electric field generator apparatus, for therapeutic use, comprising:

monitoring means for determining the heartbeat frequency of the user;

one or more generating means to generate a first signal and a second signal, wherein the frequency of the first signal is dependent upon the determined heartbeat frequency, and the frequency of the second signal simulates brain activity of a user; and means for outputting the signal as an electric field.

2. A field generator apparatus as claimed in claim 1 wherein said generating means comprises first and second signal generators for generating the first and second signals and a signal mixing means for combining said first and second signals.

3. A field generator apparatus as claimed in claim 1 wherein the second signal is a train of pulses each having a width substantially equal to the width of a neuron depolarization pulse.

4. A field generator apparatus as claimed in claim 3 wherein the train of pulses is generated at a frequency of up to 100 Hz.

5. A field generator apparatus as claimed in claim 3 wherein the width of each pulse is about 125 microseconds.

6. A field generator apparatus as claimed in claim 1 wherein the output means comprises an antenna.

7. A field generator apparatus as claimed in claim 1 wherein the output means comprises a coil.

8. A field generator apparatus as claimed in claim 1 wherein the heartbeat frequency monitoring means comprises a field effect type microphone.

9. A field generator apparatus as claimed in claim 7 wherein the heartbeat frequency monitoring means comprises an infra-red emitter and detector.

\* \* \* \* \*